United States Patent [19]

Miles

[11] 3,974,217

[45] Aug. 10, 1976

[54] PREPARATION OF SUBSTITUTED PHENYL PHOSPHONOUS DICHLORIDES

[75] Inventor: James A. Miles, Olivette, Mo.

[73] Assignee: Monsanto Company, St. Louis, Mo.

[22] Filed: July 31, 1974

[21] Appl. No.: 493,301

[52] U.S. Cl. .............................................. 260/543 P
[51] Int. Cl.$^2$ ............................................. C07F 9/46
[58] Field of Search ................................. 260/543 P

[56] References Cited
UNITED STATES PATENTS 3,294,745   12/1966   Wismer ........................... 260/543 P

OTHER PUBLICATIONS

Frank, Chem. Rev. 61 (1961) pp. 389, 390, 397–399.
Viout C. A. 50 7077–7079 (1956).
Protopopov et al, Zhurnal Obshchei Khimii 34 (5) pp. 1446–1449 (1964).

Primary Examiner—Norman Morgenstern
Attorney, Agent, or Firm—Richard H. Shear; Donald W. Peterson

[57] ABSTRACT

Alkoxy and alkylthio substituted phenyl phosphonous dichlorides are prepared by a process employing stannic chloride, titanium tetrachloride or mixtures thereof as catalyst.

11 Claims, No Drawings

PREPARATION OF SUBSTITUTED PHENYL PHOSPHONOUS DICHLORIDES

This invention relates to an improved process for the preparation of compounds of phosphorus and more particularly to an improved process for the preparation of substituted phenyl phosphonous dichlorides, sometimes referred to as substituted phenyl dichlorophosphines.

Substituted phenyl phosphonous dichorides are valuable compositions that can be used as plasticizers, as flame retardants, and as reaction intermediates in the production of a wide variety of useful compositions such as pesticides, fuel and oil additives, and the like. Heretofore, however, there has been no satisfactory economic method for the production of alkoxy and alkylthio substituted compositions. To illustrate, some preparations of arylphosphine halides include the conversion of primary phosphinic acids to arylphosphine halides by reaction with phosphorus trichloride, as disclosed by Frank, J. Org. Chem. 26, 850 (1961). Another preparation of arylphosphine halides was disclosed by Becker in U.S. Pat. No. 3,036,132. This method involved the reaction of phosphorus trichloride with M(ALR$_4$), where M is an alkali metal and R is aryl. Maier, in Helv. Chim. Acta, 46, 2026 (1963), reported the reaction of elemental phosphorus with bromobenzene at 350°C. to obtain diphenylphosphine bromide and phenylphosphine dibromide, both in very low yield. In U.S. Pat. No. 3,057,917, Maier disclosed another method for the production of arylphosphine halides. Weinberg disclosed an improved method of preparation in U.S. Pat. No. 3,557,204. None of these prior art processes provide a process for the preparation of alkoxy and thioalkyl substituted phenyl dichlorophosphines. The earliest known work to prepare one of these latter compounds from anisole was reviewed by Viout-Lesfauries in Journal des Recherches du C.N.R.S. No. 28, pages 15 to 31 in September, 1954. The abstract appears in Volume 50 (1956) of Chemical Abstracts at Columns 7077 – 7079. The reported new process employed ferric chloride as a catalyst but gave only a low yield of product.

Viout-Lesfauries describes the ferric chloride process to be an improvement over the process of Michaelis employing aluminum chloride. Aluminum chloride readily forms complexes with PCl$_3$. The complex makes the separation of pure product so difficult that a commercial operation of an aluminum chloride process is not feasible. Viout-Lesfauries reports that ferric chloride, although giving a low yield, does not complex with PCl$_3$ and hence gave fairly encouraging results. Protopopov and Kraft reported in Zhurnal Obshchei Khimii, Vol. 34, No. 5, pages 1446 – 1449, May, 1964, Reaction of m-Dimethoxybenzene with Phosphorous Trichloride, the use of ZnCl$_2$ in the reaction of meta-dimethoxybenzene with phosphorous trichloride. The ZnCl$_2$ process was proposed as an improvement over the FeCl$_3$ process which gave only low yields of product from the reaction. However, the Russians encountered purification problems noting that polycondensation occurs particularly readily in the presence of even traces of zinc chloride and found it necessary to remove ZnCl$_2$ from the reaction mixture before the mixture is distilled.

In contrast, the process of the present invention prepares a variety of easily purified alkoxy and alkylthio substituted phenyl dichlorophosphines in high yield. The present process comprises the reaction, in the presence of stannic chloride, titanium tetrachloride or mixtures thereof of phosphorous trichloride (PCl$_3$) and a compound of the formula

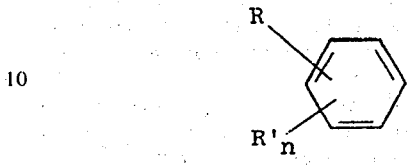

wherein R is lower alkoxy or lower alkylthio and each R' is independently lower alkyl, lower alkoxy or lower alkylthio and $n$ is an integer from 0 to 2, inclusive, provided that when $n$ is 1, the position on the benzene ring para to R is occupied by hydrogen further provided that, when $n$ is 2, no more than 2 lower alkoxy or lower alkylthio groups are positioned on adjacent carbon atoms of the benzene ring and at least two adjacent carbon atoms of the benzene ring have hydrogen substituents, to prepare substituted phenyl dichlorophosphines in which one of the hydrogens on the benzene ring is replaced by the group —PCl$_2$.

As employed herein, the terms "lower alkyl", "lower alkoxy" and "lower alkylthio" designate those groups wherein the aliphatic chain is straight or branched and has from 1 through 4 carbons, inclusive.

The reaction mass in the process of the present invention usually consists of the reactants, catalyst and the products of the reaction. As the reaction progresses, the composition of the mass will vary as the reactants are consumed and products are produced. Although solvents, organic liquids which are inert under the reaction conditions but in which one or more of the reactants or products are soluble, may be present, it is preferable to limit the starting materials to reactants and catalyst.

Water is substantially excluded from the reaction mass. Although the reaction will take place in the presence of small amounts of water, substantially anhydrous conditions are preferable to minimize catalyst and yield losses by undesired side reactions with water. A useful means employed to minimize the presence of water is conduct of the process of the invention in an inert atmosphere. Although an atmosphere of any gas which is inert under reaction conditions may be employed, such as xenon, argon, krypton, neon, helium, hydrogen chloride and nitrogen, nitrogen is preferred.

The reaction may be conducted in an open or closed system. Since hydrogen chloride gas is produced in the process, it is preferred that pressure relief means should be provided when operating in a closed system. The process is preferably conducted under reflux conditions which allow the hydrogen chloride gas to exit the system.

The process can be conducted with or without the use of agitation. Agitation of the reaction mass is preferred. The manner of agitation is not critical. It is preferred that agitation be sufficient to avoid stratification of the catalyst and the reactants.

The temperature under which the process is conducted will vary with the amount of catalyst present, the desired rate of reaction and other considerations. Since the rate of reaction increases with increases in temperature, the process is usually conducted above room temperature, i.e. about 23° Centigrade (°C.). A preferred temperature range for the reaction mass is from 40°C. to 110°C. A more preferred temperature range is from 60°C. to 105°C.

The process is usually conducted at about atmospheric pressure. However, higher or lower pressures can be used. Pressure is not a critical condition of the present process. A preferred pressure range is from 0.1 to 10 atmospheres. A more preferred pressure range is from 0.5 to 5 atmospheres.

The process is most conveniently carried out in an excess of phosphorus trichloride. The phosphorus trichloride, when present in excess, as well as being a reactant provides a medium in which the chemical reaction takes place. The molar ratio of phosphorus trichloride to substituted phenyl is not critical to the present process. Optimum yields are obtained when the ratio of phosphorus trichloride to substituted phenyl at the initiation of the reaction is from about 1/1 to about 5/1, more particularly from about 2/1 to about 4/1.

The molar ratio of catalyst, i.e. stannic chloride or titanium tetrachloride, to substituted phenyl is likewise not critical to the process. Best results are obtained with a catalyst to substituted phenyl ratio of from 0.001/1 to 1/1, more preferably from 0.005/1 to 0.1/1, still more preferably from 0.01/1 to 0.03/1.

Although the present process is usually conducted in the presence of either stannic chloride or titanium tetrachloride, mixtures of $SnCl_4$ and $TiCl_4$ work equally well. Since each component of the mixture is substantially equal in effectiveness as a catalyst for the reaction of the present process, the proportions of the two compounds in the mixture are not critical to the practice of the invention. This ability to use the two catalysts in any proportion as a mixed catalyst is of significance to the commercial practice of the invention since changeover from one catalyst to the other may be accomplished without any interruption of the process to clean out the reactor.

The process can be conducted as a batch process or in the continuous mode.

The process of the present invention can be described by the following chemical equation:

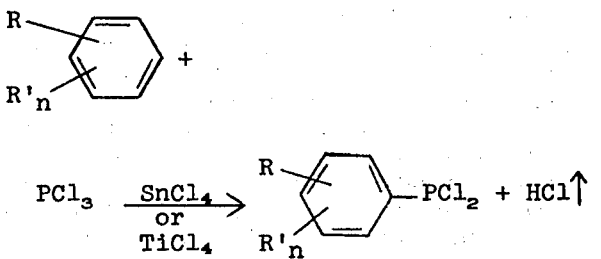

wherein R, R' and n are as defined hereinbefore. The process is more fully illustrated by the following detailed examples.

EXAMPLE 1

To a suitable reaction vessel are added 10.8 grams (g.), 0.1 mol, of anisole, 7.8 g., 3.4 milliliters (ml.) or 0.03 mol, of $SnCl_4$ and 41 g., 0.3 mol, of $PCl_3$. The vessel, under a nitrogen atmosphere, is heated on a steam bath so that the mass is refluxed for 14 hours. 5.0 grams of $SnCl_4$ is added and the reaction mass, under a nitrogen atmosphere, is heated to 100°C. for an additional 24 hours. 5.0 grams of $SnCl_4$ is added and the reaction mass, under a nitrogen atmosphere, is refluxed for an additional 30 hours. Solid material is removed by filtration through glass wool. The remaining liquid is concentrated by evaporation. The residue is distilled to give a colorless oil with a boiling point of 83° to 86°C. at 0.05 millimeters of mercury, mm of Hg, in the amount of 19 g. or 91% by weight yield. The structure of the product is confirmed by nuclear magnetic resonance and the product is identified as para-anisylphosphonous dichloride

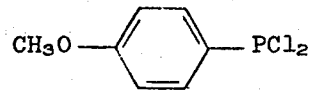

EXAMPLE 2

To a suitable reaction vessel are added 10.8 g., 0.1 mol, of anisole, 41 g., 26 ml. or 0.3 mol, of $PCl_3$ and 9.4 g., 5.4 ml. or 0.05 mol, of $TiCl_4$. The combined materials are refluxed for 64 hours under a nitrogen atmosphere. It is determined that the reaction is about 58 percent complete. Distillation recovers 2.6 g. of anisole and 4.0 g. of para-anisylphosphonous dichloride. The nuclear magnetic resonance curve is the same as from the compound prepared in Example 1 and the product compound boils at 105° to 110°C. at 0.20 mm of Hg. The product is identified as para-anisylphosphonous dichloride.

EXAMPLE 3

To a suitable reaction vessel are added 62 g., 0.5 mol, of thioanisole, 130 ml., 1.5 mol, of $PCl_3$ and 32 g. of $SnCl_4$. The vessel, under a nitrogen atmosphere, is heated on a steam bath to bring the mass to reflux. After 40 hours, an additional 5 g. of $SnCl_4$ is added and reflux is continued. After 90 hours, an additional 6 ml. of $SnCl_4$ is added. After 150 hours at reflux, the reaction mass is cooled to room temperature. Solid crystals which form on cooling are removed by filtration. The filtrate is extracted with petroleum ether. Concentration of the petroleum ether extracts leaves an orange oil. The orange oil is distilled and 35 g. of unreacted raw materials and catalyst is recovered and 17.5 g. of product is isolated. The product has a boiling point of 98° to 103°C. at 0.02 mm of Hg and is identified, confirmed by nuclear magnetic resonance, as para-thioanisylphosphonous dichloride.

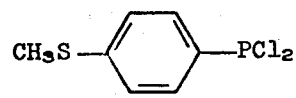

EXAMPLE 4

To a suitable reaction vessel are added 13.8 g., 0.1 mol, of meta-dimethoxybenzene, 41 g. of $PCl_3$ and 6.0 g., 0.04 mol, of $SnCl_4$. The vessel, under a nitrogen atmosphere, is heated on a steam bath to bring the mass to reflux. After 15 hours at reflux, the mass is distilled to give 7 g. of a yellow oil with a boiling point range of 115° to 135°C. at 1 mm of Hg. Redistillation gives 4.5 g. of a colorless oil with a boiling point range of 104° to 106°C. at 0.2 mm of Hg. The product is identified, confirmed by nuclear magnetic resonance, as 3,4-dimethoxyphenylphosphonous dichloride.

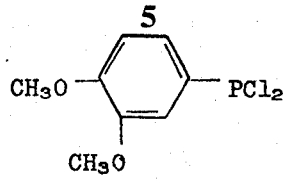

Empirical Formula — $C_8H_9O_2PCl_2$

| Element | Elemental Analysis Calculated | Found |
|---|---|---|
| C | 40.04 | 40.13 |
| H | 3.86 | 3.81 |
| Cl | 29.78 | 29.78 |

EXAMPLE 5

To a suitable reaction vessel are added 12.2 g., 0.1 mol, of ortho-methylanisole, 41 g., 0.3 mol, of PCl₃ and 6.9 g. of SnCl₄. The vessel, under a nitrogen atmosphere, is heated on a steam bath to bring the mass to reflux. After 15 hours at reflux, the reaction mass is cooled to room temperature. Solid crystals which form on cooling are removed by filtration. The filtrate is concentrated on an evaporator. The residue is distilled and the product having a boiling point of 103° to 105°C. at 0.07 mm of Hg is recovered with a yield of 68 mol weight percent and is identified, confirmed by nuclear magnetic resonance, as 3-methyl-para-anisylphosphonous dichloride.

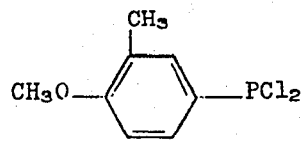

EXAMPLE 6

To a suitable reaction vessel are added 19.8 g., 0.162 mol, of ortho-methylanisole, 40 ml., of PCl₃ and 10 g. of SnCl₄. The vessel, under a nitrogen atmosphere, is heated on a steam bath to bring the mass to reflux. After 20 hours at reflux, the reaction mass is cooled to room temperature. Solid crystals which form on cooling are removed by filtration. Concentration of the filtrate leaves 35 g. of an orange oil. The orange oil is distilled and 1.6 grams of unreacted raw material is recovered and 25.5 g. of product is isolated. Yield is calculated to be 79 mol weight percent. The product has a boiling point of 107° to 110°C. at 0.07 mm of Hg and is identified, confirmed by nuclear magnetic resonance, as 3-methyl-para-anisylphosphonous dichloride.

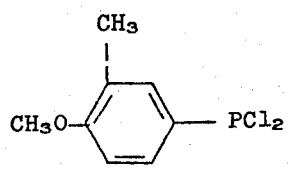

Empirical Formula — $C_8H_9OPCl_2$

| Element | Elemental Analysis Calculated | Found |
|---|---|---|
| C | 43.10 | 43.23 |
| H | 4.07 | 4.10 |
| Cl | 31.94 | 32.03 |

EXAMPLE 7

To a suitable reaction vessel containing a nitrogen atmosphere are added 10.2 g., 0.084 mol, of meta-methylanisole, 34 g., 0.25 mol, of PCl₃ and 7.8 g., 3.5 ml. or 0.03 mol, of SnCl₄. The vessel is heated on a steam bath to bring the mass to reflux under the nitrogen atmosphere. After 18 hours, an additional 3 g. of SnCl₄ is added and reflux is continued.

After an additional 24 hours at reflux, the reaction mass is cooled to room temperature. White solid crystals which form are removed by filtration. The filtrate is distilled and 9.0 g. of product is isolated. The product has a boiling point of 93° to 97°C. at 0.1 mm of Hg and is identified as a mixture of about equal parts of two isomers, confirmed by nuclear magnetic resonance, 2-methyl-para-anisylphosphonous dichloride and 4-methyl-ortho-anisylphosphonous dichloride.

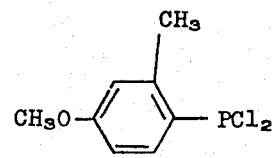

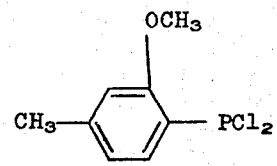

EXAMPLE 8

To a suitable reaction vessel containing a nitrogen atmosphere are added 40.2 g., 0.33 mol, of meta-methylanisole, 81 ml., 1.0 mol, of PCl₃ and 34 g., 0.15 mol, of SnCl₄. The vessel is heated on a steam bath to bring the mass to reflux under the nitrogen atmosphere. After 40 hours, an additional 5 g. of SnCl₄ is added and reflux is continued. After 90 hours, an additional 6 g. of SnCl₄ is added. After 32 hours at reflux, the reaction mass is cooled to room temperature and diluted with petroleum ether. Solid crystals which form are removed by filtration. Concentration of the mass leaves 80 g. of an orange oil. The orange oil is vacuum distilled and 32 g. of product is isolated. The pale yellow oil product has a boiling point of 102° to 105°C. at 0.08 mm of Hg and is identified as a mixture of about equal parts of the same two isomers as found in Example 7, confirmed by nuclear magnetic resonance.

EXAMPLE 9

The procedure of Example 8 is repeated using the following material, quantities and reflux time:

| meta-methyl anisole | 100 g. |
| PCl₃ | 200 ml. |

| | -continued | |
|---|---|---|
| SnCl₄ | | 35 ml. |
| Reflux Time | | 72 hours |

60 g. of the same mix of isomers as prepared in Examples 7 and 8 is obtained.

EXAMPLE 10

To a suitable reaction vessel are added 14.5 g. of 2,3-dimethylanisole, 27 ml., of PCl₃ and 2 ml. of SnCl₄. The vessel, under a nitrogen atmosphere, is heated on a steam bath to bring the mass to reflux. After 18 hours, an additional 2 ml. of SnCl₄ is added and reflux is continued. After 90 hours at reflux, the reaction mass is vacuum distilled and 16.9 g. of product is isolated. The product has a boiling point of 108° to 111°C. at 0.09 mm of Hg and is identified, confirmed by nuclear magnetic resonance, as 2,3-dimethyl-para-anisylphosphonous dichloride.

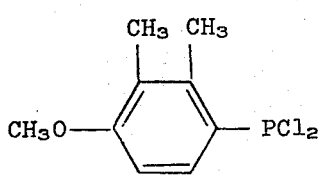

Empirical Formula — $C_9H_{11}Cl_2OP$

| | Elemental Analysis | |
|---|---|---|
| Element | Calculated | Found |
| C | 45.60 | 45.73 |
| H | 4.64 | 4.78 |
| Cl | 29.99 | 29.81 |

EXAMPLES 11 THROUGH 13

Following substantially the procedure of Example 10, the process is conducted with a variety of reactants to illustrate the difference in yield when employing a representative example of the catalysts disclosed herein in the process of the present invention and a prior art catalyst, i.e. FeCl₃.

| Example | Product | Catalyst | Mol Percent Yield |
|---|---|---|---|
| 11 | para-anisyl phosphonous dichloride | (a) SnCl₄ (b) FeCl₃ | 95 31 |
| 12 | para-thioanisyl phosphonous dichloride | (a) SnCl₄ (b) FeCl₃ | 36–40 10–15 |
| 13 | 2,4-dimethoxyphenyl phosphonous dichloride | (a) SnCl₄ (b) FeCl₃ | 50 20 |

Examples 11 through 13 conducted with TiCl₄ catalyst gives substantially the same yields as with the SnCl₄ catalyst. Examples 11 through 13 conducted with a catalyst of 50 percent by weight SnCl₄ and 50 percent by weight TiCl₄ gives substantially the same yield as the individual catalysts alone. Examples 11 through 13 conducted with a ZnCl₂ catalyst forms a tarry polymer during separation so that no yield is determined. Examples 11 through 13 conducted with a AlCl₃ catalyst forms a tarry mass so that no yield is determined.

EXAMPLES 14 THROUGH 16

Following substantially the process of Example 10 and employing SnCl₄ as catalyst, the products of these examples are obtained in the yields shown:

| Example | Starting Material | Product | Yield |
|---|---|---|---|
| 14 | Para-propoxy- benzene | para-propoxyphenyl phosphonous dichloride | 70 |
| 15 | 3-tertiary butylanisole | 2-methoxy-4-tertiary-butyl- phenyl phosphonous dichloride | 41 |
| 16 | 3-isopropyl- anisole | 2-methoxy-4-isopropyl- phenyl-phosphonous di- chloride, 2-isopropyl-4- methoxyphenyl-phospho- nous dichloride (75:25 mixture) | 55 |

Employing TiCl₄ as catalyst in the processes of Examples 14, 15 and 16, the same products in substantially the same yields are obtained.

EXAMPLES 17 THROUGH 24

Examples 17 through 24 illustrate additional products which are similarly prepared by the process of this invention.

| Example | Starting Material | Product |
|---|---|---|
| 17 | Ethoxybenzene | Para-ethoxyphenyl phosphonous dichloride |
| 18 | Butoxybenzene | Para-butoxyphenyl phosphonous dichloride |
| 19 | 2,3-diethylanisole | 2,3-diethyl-para-anisyl phosphonous dichloride |
| 20 | 2,5-dipropylethoxy- benzene | 2,5-dipropyl-4-ethoxyphenyl phosphonous dichloride |
| 21 | Propylthiobenzene | Para-propylthiophenyl phosphonous dichloride |
| 22 | Isobutylthio- benzene | Para-isobutylthiophenyl phosphonous dichloride |
| 23 | Meta-dimethylthio- benzene | 2,4-dimethylthiophenyl phosphonous dichloride |
| 24 | Ortho-methyl- methylthiobenzene | 3-methyl-4-methylthiophenyl phosphonous dichloride |

Each of the compounds prepared by the process of the present invention will slowly hydrolyze in moist air.

What is claimed is:

1. A process for the preparation of substituted phenyl phosphonous dichlorides comprising the reaction of a substituted phenyl compound of the formula

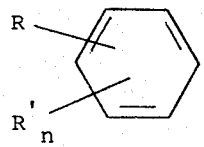

wherein R is lower alkoxy or lower alkylthio and each R' is independently lower alkyl, lower alkoxy or lower alkylthio and n is an integer from 0 to 2, inclusive, provided that, when n is 1, the position on the benzene ring para to R is occupied by hydrogen further provided that, when $n$ is 2, no more than 2 lower alkoxy or lower alkylthio groups are positioned on adjacent carbon atoms of the benzene ring and at least two adjacent carbon atoms of the benzene ring have hydrogen substituents and phosphorous trichloride in the presence of stannic chloride.

2. A process of claim 1 wherein the catalyst is stannic chloride.

3. A process of claim 1 wherein the reaction is conducted at a temperature above room temperature but no higher than the reflux temperature of the reaction mass.

4. A process of claim 3 wherein the reaction is conducted at reflux.

5. A process of claim 1 wherein $n$ is 0.

6. A process of claim 1 wherein $n$ is 1.

7. A process of claim 1 wherein $n$ is 2.

8. A process of claim 1 wherein said phosphorous trichloride is present in molar excess of said substituted phenyl.

9. A process of claim 1 wherein the molar ratio of phosphorous trichloride to substituted phenyl ranges from about 2:1 to 4:1.

10. A process of claim 1 wherein the molar ratio of said catalyst to said substituted phenyl ranges from about 0.005:1 to 0.1:1.

11. A process of claim 1 wherein the reaction is conducted in an inert atmosphere.

* * * * *